(12) United States Patent
Dotzauer et al.

(10) Patent No.: US 10,280,386 B2
(45) Date of Patent: *May 7, 2019

(54) ENHANCED PEROXYGEN STABILITY IN MULTI-DISPENSE TAED-CONTAINING PEROXYGEN SOLID

(71) Applicant: Ecolab USA Inc., Saint Paul, MN (US)

(72) Inventors: David Dotzauer, St. Paul, MN (US); Krista Kutz, Bloomington, MN (US)

(73) Assignee: Ecolab USA Inc., Saint Paul, MN (US)

( * ) Notice: Subject to any disclaimer, the term of this patent is extended or adjusted under 35 U.S.C. 154(b) by 10 days.

This patent is subject to a terminal disclaimer.

(21) Appl. No.: 14/678,055

(22) Filed: Apr. 3, 2015

(65) Prior Publication Data

US 2016/0289606 A1    Oct. 6, 2016

(51) Int. Cl.
*C11D 3/395*    (2006.01)
*D21C 9/16*    (2006.01)
(Continued)

(52) U.S. Cl.
CPC ........ *C11D 3/3953* (2013.01); *A47L 15/0002* (2013.01); *A61L 2/18* (2013.01); *C02F 1/722* (2013.01); *C07D 301/02* (2013.01); *C11D 1/22* (2013.01); *C11D 3/044* (2013.01); *C11D 3/225* (2013.01); *C11D 3/33* (2013.01); *C11D 3/361* (2013.01); *C11D 3/3917* (2013.01);
(Continued)

(58) Field of Classification Search
CPC .................................. C11D 1/83; C11D 1/29
USPC ......................... 510/218, 445, 471
See application file for complete search history.

(56) References Cited

U.S. PATENT DOCUMENTS 4,259,200 A    3/1981  Sims et al.
4,619,779 A    10/1986  Hardy
(Continued)

FOREIGN PATENT DOCUMENTS

CA    1207955    7/1986
CA    1264327    1/1990
(Continued)

OTHER PUBLICATIONS

Clinell "Sporicidal Wipes", two pages, http://www.clinell.com/sporicidal-wipes, retrieved from Internet on Feb. 12, 2015.
(Continued)

*Primary Examiner* — Nicole M. Buie-Hatcher
*Assistant Examiner* — M. Reza Asdjodi
(74) *Attorney, Agent, or Firm* — McKee, Voorhees & Sease, PLC

(57) ABSTRACT

Stabilized compositions employing a sequestrant system and a binding system for improving shelf stability and dispensing stability of a solid activated bleach composition are disclosed. The compositions contain a peroxygen source and a catalyst activator which require generation of a peroxycarboxylic acid or other active oxygen sanitizing agent at a point of use. Stabilized compositions employ a sequestrant system including a phosphonic acid and/or dipicolinic acid sequestrant and a binding system comprising an anionic surfactant for a solid formulation of a catalyst activator and peroxygen source to provide shelf stability and dispensing stability for a activated bleach composition. Methods of formulating and use are further disclosed.

19 Claims, 1 Drawing Sheet

(51) Int. Cl.

| | |
|---|---|
| *A47L 15/00* | (2006.01) |
| *A61L 2/18* | (2006.01) |
| *C02F 1/72* | (2006.01) |
| *C07D 301/02* | (2006.01) |
| *D06F 35/00* | (2006.01) |
| *D21C 9/10* | (2006.01) |
| *D21H 21/32* | (2006.01) |
| *C11D 1/22* | (2006.01) |
| *C11D 3/04* | (2006.01) |
| *C11D 3/22* | (2006.01) |
| *C11D 3/33* | (2006.01) |
| *C11D 3/36* | (2006.01) |
| *C11D 3/39* | (2006.01) |
| *C11D 17/00* | (2006.01) |
| *C02F 101/10* | (2006.01) |
| *C02F 101/38* | (2006.01) |
| *C02F 103/10* | (2006.01) |
| *C11D 3/10* | (2006.01) |

(52) U.S. Cl.
CPC ........ *C11D 17/0052* (2013.01); *D06F 35/005* (2013.01); *D21C 9/1063* (2013.01); *D21C 9/16* (2013.01); *D21H 21/32* (2013.01); *C02F 2101/101* (2013.01); *C02F 2101/105* (2013.01); *C02F 2101/38* (2013.01); *C02F 2103/10* (2013.01); *C02F 2303/02* (2013.01); *C02F 2303/04* (2013.01); *C02F 2305/04* (2013.01); *C11D 3/10* (2013.01)

(56) References Cited

U.S. PATENT DOCUMENTS

| | | | |
|---|---|---|---|
| 4,681,695 A | 7/1987 | Divo | |
| 4,853,143 A | 8/1989 | Hardy et al. | |
| 5,225,100 A | 7/1993 | Fry et al. | |
| 5,246,612 A | 9/1993 | Van Dijk et al. | |
| 5,302,310 A | 4/1994 | Houghton | |
| 5,468,410 A | 11/1995 | Angevaare et al. | |
| 5,705,466 A | 1/1998 | Baillely et al. | |
| 5,792,738 A | 8/1998 | Baillely et al. | |
| 5,858,949 A | 1/1999 | Moschner | |
| 5,965,505 A | 10/1999 | Baillely et al. | |
| 5,981,463 A * | 11/1999 | Oberlander | C11D 1/72 |
| | | | 510/224 |
| 6,017,871 A | 1/2000 | Baeck et al. | |
| 6,022,490 A | 2/2000 | Hermant et al. | |
| 6,187,739 B1 | 2/2001 | Merz et al. | |
| 6,194,368 B1 | 2/2001 | Waschenbach et al. | |
| 6,391,840 B1 | 5/2002 | Thompson et al. | |
| 6,399,577 B1 | 6/2002 | Filbin | |
| 6,417,151 B1 | 7/2002 | Grothus et al. | |
| 6,440,926 B1 * | 8/2002 | Spadoni | A23L 2/40 |
| | | | 510/276 |
| 6,514,509 B2 | 2/2003 | Tabasso | |
| 6,551,975 B1 | 4/2003 | Baker et al. | |
| 6,551,983 B1 | 4/2003 | Welch et al. | |
| 6,583,098 B1 | 6/2003 | Cassie | |
| 6,689,739 B1 | 2/2004 | Hall | |
| 7,271,137 B2 | 9/2007 | Tucker et al. | |
| 7,470,655 B2 | 12/2008 | Biering et al. | |
| 7,524,804 B2 | 4/2009 | Kaneda et al. | |
| 7,563,758 B2 | 7/2009 | Dicosimo et al. | |
| 7,654,321 B2 | 2/2010 | Zazovsky et al. | |
| 7,786,065 B2 | 8/2010 | Hecht et al. | |
| 7,939,485 B2 | 5/2011 | Price et al. | |
| 7,967,220 B2 | 6/2011 | Hansen et al. | |
| 8,206,963 B2 | 6/2012 | Dicosimo et al. | |
| 8,206,964 B2 | 6/2012 | DiCosimo et al. | |
| 8,222,012 B2 | 7/2012 | DiCosimo et al. | |
| 8,338,352 B2 * | 12/2012 | Tjelta | C11D 3/10 |
| | | | 510/191 |
| 8,414,793 B2 | 4/2013 | Abrams et al. | |
| 8,633,148 B2 | 1/2014 | Smets et al. | |
| 8,815,789 B2 | 8/2014 | Tetard et al. | |
| 8,822,402 B2 | 9/2014 | Smets et al. | |
| 8,877,240 B1 | 11/2014 | Moore | |
| 2002/0198128 A1 | 12/2002 | Perkins et al. | |
| 2003/0109403 A1 * | 6/2003 | Man | C11D 3/046 |
| | | | 510/367 |
| 2005/0233920 A1 | 10/2005 | Stolte et al. | |
| 2006/0293204 A1 * | 12/2006 | Kaneda | C11D 3/222 |
| | | | 510/376 |
| 2007/0082832 A1 | 4/2007 | DiCosimo et al. | |
| 2008/0045593 A1 | 2/2008 | Kaiser et al. | |
| 2009/0176687 A1 * | 7/2009 | Tjelta | C11D 3/10 |
| | | | 510/445 |
| 2009/0181874 A1 | 7/2009 | Souter et al. | |
| 2009/0258042 A1 | 10/2009 | Anastasiou et al. | |
| 2011/0118166 A1 * | 5/2011 | Tjelta | C11D 3/10 |
| | | | 510/219 |
| 2011/0177145 A1 | 7/2011 | Erkenbrecher, Jr. et al. | |
| 2011/0245136 A1 | 10/2011 | Smets et al. | |
| 2012/0083437 A1 | 4/2012 | Choczaj et al. | |
| 2012/0231990 A1 * | 9/2012 | Besse | C11D 3/10 |
| | | | 510/445 |
| 2012/0322708 A1 | 12/2012 | Lant et al. | |
| 2015/0361383 A1 * | 12/2015 | Dotzauer | B01J 31/2295 |
| | | | 510/218 |

FOREIGN PATENT DOCUMENTS

| | | |
|---|---|---|
| CA | 2155636 | 8/1994 |
| CA | 2569025 | 6/2008 |
| DE | 19713851 A1 | 10/1998 |
| DE | 202008009873 U1 | 11/2008 |
| DE | 102008064481 A1 | 8/2010 |
| DE | 102010028008 A1 | 10/2011 |
| EP | 0132860 A1 | 2/1985 |
| EP | 0534772 | 3/1993 |
| EP | 0699080 | 3/1996 |
| EP | 0737738 A3 | 10/1996 |
| EP | 0826414 A2 | 3/1998 |
| EP | 0826414 A3 | 3/1998 |
| EP | 1165742 B1 | 1/2002 |
| EP | 1228190 B1 | 8/2002 |
| EP | 1726636 A1 | 11/2006 |
| EP | 1726636 B1 | 11/2006 |
| EP | 1755387 B1 | 2/2007 |
| JP | 2813167 | 12/1996 |
| WO | 9401521 | 1/1994 |
| WO | 9426317 | 11/1994 |
| WO | 9505444 | 2/1995 |
| WO | 9521236 | 8/1995 |
| WO | 9528464 | 10/1995 |
| WO | 9528465 | 10/1995 |
| WO | 9711150 | 3/1997 |
| WO | 9825468 | 6/1998 |
| WO | 9839405 | 9/1998 |
| WO | 9839406 | 9/1998 |
| WO | 9962472 | 12/1999 |
| WO | 0051656 | 9/2000 |
| WO | 0244314 | 6/2002 |
| WO | 03106611 | 12/2003 |
| WO | 2005056782 | 6/2005 |
| WO | 2007070609 | 6/2007 |
| WO | 2007106293 | 9/2007 |
| WO | 2008005571 | 1/2008 |
| WO | 2009067279 | 5/2009 |
| WO | 2010035199 | 4/2010 |
| WO | 2010039953 | 4/2010 |
| WO | 2010039956 | 4/2010 |
| WO | 2010039958 | 4/2010 |
| WO | 2010039960 | 4/2010 |
| WO | 2010039961 | 4/2010 |
| WO | 2011027170 | 3/2011 |
| WO | 2011146557 | 11/2011 |
| WO | 2012004772 | 1/2012 |
| WO | 2012012494 | 1/2012 |

(56) References Cited

FOREIGN PATENT DOCUMENTS

| WO | 2012175401 | 12/2012 |
| WO | 2014139577 | 9/2014 |
| WO | 2014166514 | 10/2014 |

OTHER PUBLICATIONS

Clinell, "The Most Clinically Proven Disinfectant Wipe in the World", 8 pages, date unknown.
JP 2813167—published Oct. 22, 1998—English Translation.
International Searching Authority, PCT/US2016/025501, "The International Search Report and the Written Opinion", dated Jun. 22, 2016, 11 pages.
International Searching Authority, PCT/US2016/025497 filed Apr. 1, 2016, "The International Search Report and the Written Opinion of the International Searching Authority", 12 pages, dated Jul. 10, 2016.

\* cited by examiner

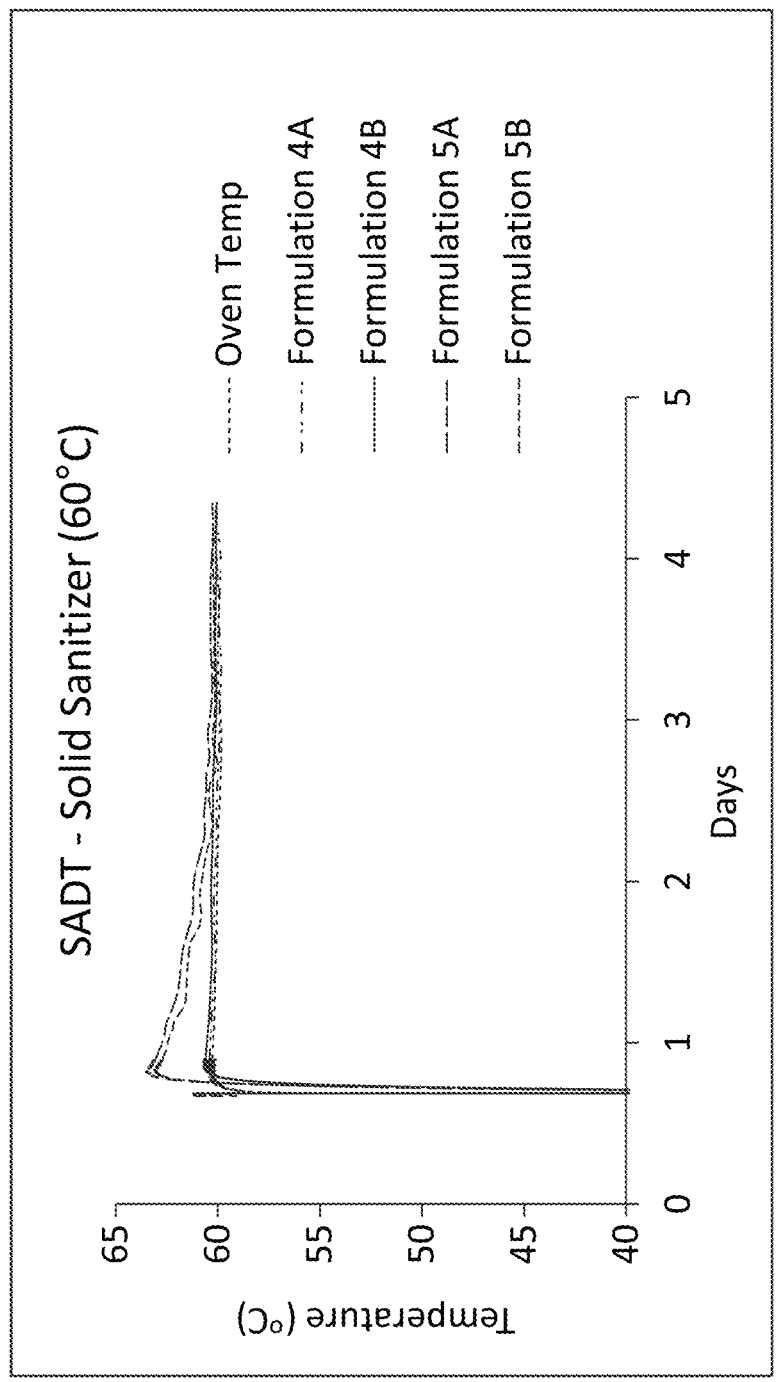

ENHANCED PEROXYGEN STABILITY IN MULTI-DISPENSE TAED-CONTAINING PEROXYGEN SOLID

CROSS-REFERENCE TO RELATED APPLICATIONS

This application is related to U.S. patent application Ser. No. 14/678,081, filed simultaneously herewith and entitled Enhanced Peroxygen Stability using Anionic Surfactant in TAED-Containing Peroxygen Solid. The entire contents of this patent application are hereby expressly incorporated herein by reference including, without limitation, the specification, claims, and abstract, as well as any figures, tables, or drawings thereof.

FIELD OF THE INVENTION

The invention relates to solid, stabilized peroxygen bleach compositions, namely multi-use or multi-dispense solid compositions. The solid compositions employ a binding system and sequestrant for improving shelf stability of an activated bleach composition, and allowing multi-dispensing of the solid composition, containing a peroxygen source and a bleach activating agent. Beneficially, the stabilized compositions allow solid formulation and delivery for oxygen bleaches, in addition to the liquid, powder and solid blocks which are currently offered for chlorine sanitizers. Stabilized compositions employ a sequestrant and a binding system containing an anionic surfactant. In particular, the bleach activating agent is combined with the sequestrant and binding system providing shelf stability of the activated bleach composition to prevent premature reaction of reactive components during storage and/or transportation, as well as during multi-dispensing for prolonged periods of time, thereby allowing both reactive components to be formulated into a single solid composition. Methods of formulating and methods of use are further provided.

BACKGROUND OF THE INVENTION

The use of active oxygen sources (e.g. peroxide) with a transition metal catalyst is known to improve bleaching performance; see for example U.S. Pat. No. 5,246,612. Similarly, use of bleach activating agents with oxygen sources (e.g. percarbonates) are known to generate bleaching compositions at a point of use. However, the delivery of these reactive components—active oxygen sources and activator materials—in a single bleaching formulation suffers from numerous stability challenges. In particular, the components react when mixed together. Moreover, certain bleach activating agents when combined with active oxygen sources have poor available oxygen stability over time, especially at elevated storage temperatures.

Improvements to stability, as well as separating the active components to prevent premature generation of bleaching compositions have been disclosed for various bleach activating technologies. For example, the use of coatings or encapsulation of particulate materials, including the bleach activator TAED have been employed (U.S. Pat. No. 4,853,143). Moreover, the improvement in stability of bleach compositions has also included, for example, development of agglomerated forms or granules and encapsulating the same (EP 1735422), use of water soluble ligands or complexing agents (e.g. EDTA, DTPA, NTA, and alkaline metal and alkaline earth metal salts, alkaline metal tryphosphates), and/or use of biopolymers and polysaccharides to stabilize catalysts. Despite these improvements, stability concerns remain for formulating solid and/or multi-use detergent compositions containing such reactive components.

The use of bleach activating agents or catalysts with unstable oxygen sources results in limited shipment and/or storage shelf life or stability despite the various advances by those skilled in the art. The shelf life is commonly regarded as the period of time over which the product may be stored while retaining its required performance efficacy. A satisfactory shelf life is in many instances a crucial factor for the success of a commercial product. A product with a short shelf life generally dictates that the product is made in small batches and is rapidly sold to the consumer. Beneficially, products with a longer shelf life may be made in larger batches, maintained in storage for a longer period of time and/or maintained by a consumer for a longer period of time before use. There remains a clear need to increase the shelf life of a combination product containing an oxidant and a bleach activator to prevent the reaction of the active components.

Accordingly, it is an objective of the claimed invention to develop solid compositions having increased shelf life and stability when employing reactive components, such as a peroxygen source (e.g. sodium percarbonate) and a bleach activator (e.g. TAED) without requiring any encapsulation, layering of components or the like to provide physical separation of the reactive components in a solid formulation.

It is an object of the present invention to formulate solid compositions with improved stability by minimizing the interaction between reactive components, such as coatings and/or binding systems to minimize the interaction between the reactive components, such as a peroxygen source (e.g. sodium percarbonate) and a bleach activator (e.g. TAED).

A further object of the invention is to incorporate an active oxygen source and a bleach activating agent into a single solid detergent block suitable for multi-dispensing over periods of time up to 2 weeks, while beneficially overcoming the poor available oxygen stability as experienced in the prior art, including at elevated storage temperatures.

A further object of the invention is to provide methods of protection and/or formulating a bleach activator and oxygen source in a single, stabilized solid detergent block with a sequestrant and an anionic surfactant binding agent to prevent reaction of the bleach activating agent an active oxygen source (e.g. peroxygen source).

Other objects, advantages and features of the present invention will become apparent from the following specification taken in conjunction with the accompanying drawings.

BRIEF SUMMARY OF THE INVENTION

An advantage of the invention is an improved shelf stability of activated bleach compositions containing a peroxygen source and a bleach activator which will react during use to form a peroxycarboxylic acid. It is a benefit of the present invention that a bleach activator is prevented from reacting with the peroxygen source due to the presence of a sequestrant and a binding system including an anionic surfactant to prevent premature reaction between the peroxygen source and bleach activator in a solid formulation. Beneficially, the storage and/or transportation stability of the compositions are significantly increased by the presence of the binding system including an anionic surfactant, allowing both reactive components to be formulated into a single solid composition.

In an embodiment, the present invention provides a stabilized solid activated bleach composition comprising: at least one alkaline solidification matrix; an active oxygen source; a bleach activating agent; a sequestrant; and a binding system comprising an anionic surfactant and a cellulose source. In an aspect, the solid composition has less than 1 wt-% water. In a further aspect, the solid composition has shelf stability at room temperature for at least one year.

In a further embodiment, the present invention provides a stabilized solid activated bleach composition comprising: from about 10-80 wt-% of at least one alkaline solidification matrix; from about 10-75 wt-% of an active oxygen source; from about 0.1-50 wt-% of a bleach activating agent; from about 0.01-25 wt-% of a sequestrant; and from about 0.1-25 wt-% of a binding system comprising an anionic surfactant and a cellulose source. In a further aspect, the solid composition has less than 1 wt-% water in the solid composition. In a further aspect, the solid composition has shelf stability at room temperature for at least one year.

In a still further embodiment, the present invention provides methods of cleaning, sanitizing and/or bleaching comprising: providing a stabilized solid activated bleach composition; generating a use solution of the composition; and contacting a surface or object in need of cleaning, sanitizing and/or bleaching with the use solution of the composition. In an aspect, the methods of cleaning, sanitizing and/or bleaching are suitable for prolonged dispensing, such as where water is in contact with the solid composition for multi-dispensing such as required in industrial applications of use where a large solid formulation may be employed for hours to days, or from days to at least about 2 weeks.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1 shows the self-accelerating decomposition temperature (SADT) of evaluated solid bleaching compositions according to embodiments of the invention as set forth in Example 2.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The embodiments of this invention are not limited to particular activated bleach compositions employing the sequestrant and anionic surfactant-containing binding system for stabilizing a solid composition containing both a peroxygen source and catalyst activator, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism. For the purpose of this patent application, successful microbial reduction is achieved when the microbial populations are reduced by at least about 50%, or by significantly more than is achieved by a wash with water. Larger reductions in microbial population provide greater levels of protection.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Stabilized Solid Activated Bleach Compositions

Stabilized solid activated bleach compositions are provided according to the invention as an alternative to chlorine-based sanitizers. Beneficially, oxygen sanitizers (e.g. peracetic acid and other active oxygen sources) provide well documented antimicrobial efficacy for sanitizing, disinfecting and/or bleaching. A stable solid composition containing the active oxygen (e.g. peracetic acid) is not practical due to reactivity and loss of efficacy over time due to stability concerns which are well documented in the art. However, a solid formulation of a composition with the necessary reactive components to form an active oxygen (e.g. peracetic acid or other peroxycarboxylic acid) in-situ by combining hydrogen peroxide with a bleach activator (e.g. tetraacetylethylenediamine (TAED)) can be provided. According to the present invention, in order to provide a stable solid composition the hydrogen peroxide source must not react with the bleach activator. This is increasingly difficult when large block solids are formulated for multi-dispensing which creates a water interface on the solid composition and required increased stability for the solid composition. Therefore, the invention provides for a stabilized solid activated bleach composition employing a phosphonic acid and/or dipicolinic acid sequestrant and a binding system comprising an anionic surfactant to prevent a decline in available oxygen stability.

Exemplary ranges of the stabilized solid activated bleach compositions according to the invention are shown in Table 1 in weight percentage of the solid compositions. The solid compositions may comprise, consist of or consist essentially of the materials set from in Table 1. Without being limited according to the invention, all ranges for the ratios recited are inclusive of the numbers defining the range and include each integer within the defined range of ratios.

TABLE 1

| Material | First Exemplary Range wt-% | Second Exemplary Range wt-% | Third Exemplary Range wt-% | Fourth Exemplary Range wt-% |
|---|---|---|---|---|
| Bleach Activating Agent | 0.1-50 | 1-50 | 5-40 | 10-25 |
| Active Oxygen Source (e.g. percarbonate) | 10-75 | 10-50 | 20-50 | 25-50 |
| Binding System | 0.1-25 | 1-20 | 1-15 | 1-10 |
| Alkaline Solidification Matrix (e.g. alkali metal carbonate) | 10-80 | 10-70 | 15-60 | 20-40 |
| Sequestrant System | 0.01-25 | 0.1-20 | 0.5-10 | 0.5-5 |
| Additional Functional Ingredients | 0-30 | 0.1-25 | 1-20 | 5-15 |

The stabilized solid activated bleach compositions preferably are water-free or substantially water-free to maintain stability of the binding system, bleach activating agent and active oxygen source. In an aspect, the solid compositions have a water content of less than about 1% by weight, less than about 0.5% by weight, less than about 0.1% by weight, less than about 0.05% by weight, and most preferably free of water (i.e. dried). Without being limited to a particular mechanism of theory of the invention, the stabilized solid activated bleach compositions are formulated to minimize and preferably remove water, such as by formulation containing anhydrous components. In an aspect, the solid compositions have such water contents upon formulation of the solid composition, and one skilled in the art will ascertain that despite anhydrous components for various aspects of the formulation of the compositions conditions, such as for example humidity and temperature, may cause changes in the water content of the solid due to the hydroscopic nature thereof.

The stabilized solid activated bleach compositions are preferably provided as concentrate compositions which may be diluted to form use compositions. In general, a concentrate refers to a composition that is intended to be diluted with water to provide a use solution that contacts an object to provide the desired sanitizing, bleaching, or the like. The stabilized solid activated bleach composition that contacts the articles to be washed can be referred to as a concentrate or a use composition (or use solution) dependent upon the formulation employed in methods according to the invention. It should be understood that the concentration of the bleach activating agent, active oxidant, binding system, alkalinity agents for solidification and other additional functional ingredients in the stabilized solid activated bleach compositions will vary depending on the concentrated nature of the formulation and the desired use solution thereof.

In some aspects, the stabilized solid activated bleach compositions maintain shelf stability for at least about 6 months, or at least about 1 year at room temperature. Beneficially, the stabilized solid activated bleach compositions maintain shelf stability at elevated storage temperatures, including for example at temperatures up to at least 40° C. for 12 weeks or up to a at least 50° C. for 8 weeks.

In some aspects, the stabilized solid activated bleach compositions maintain stability during a multi-dispensing use, where there is a wet interface from water or a diluent contacting at least a portion of the solid, for at least a few hours to 2 weeks, or at 1 day to 2 weeks, or at least 1 week to 2 weeks. Beneficially, the stabilized solid activated bleach compositions maintain the stability during use as measured by maintained oxygen content in the solid compositions of at least about 80%.

Bleach Activating Agents

The stabilized solid activated bleach compositions according to the invention include a bleach activating agent (also referred to as an activating agent) to further increase the activity of the active oxygen source (e.g. percarbonate). Bleach activating agents can be used alone or in combination with catalysts.

Generally, bleach activating agents have the following formula: R—(C—O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767.

According to an aspect of the invention, preferred activating agents include N,N,N',N'-tetraacetyl ethylene diamine (TAED); sodium-4-benzoyloxy benzene sulphonate (SBOBS); sodium-1-methyl-2-benzoyloxy benzene-4-sulphonate; sodium-4-methyl-3-benzoyloxy benzoate; SPCC trimethyl ammonium toluyloxy benzene sulphonate; sodium nonanoyloxybenzene sulphonate, sodium 3,5,5,-trimethyl hexanoyloxybenzene sulphonate; penta acetyl glucose (PAG); octanoyl tetra acetyl glucose and benzoyl tetracetyl glucose.

Additional description of bleach activating agents is set forth, for example, in U.S. Pat. Nos. 4,853,143, 7,709,437 and 8,431,519, and EP 2021454 which are herein incorporated by reference in its entirety.

In aspects of the invention, the activating agent has a concentration in the stabilized solid activated bleach compositions from about 0.1 wt-% to about 50 wt-%, from about 1 wt-% to about 50 wt-%, from about 5 wt-% to about 40 wt-%, or from about 10 wt-% to about 25 wt-%. In some aspects the ratio of the activating agent to peroxygen source in the solid composition is in a ratio of from about 1:1 to about 1:10, from about 1:1 to about 1:5, from about 1:1 to about 1:2, and most preferably a ratio of about 1:2. It is to be understood that all values and ranges between these values and ranges are encompassed by the invention.

Active Oxygen Source

The stabilized solid activated bleach compositions according to the invention include at least one active oxygen compound. The active oxygen sources suitable for use according to the invention can be inorganic or organic, and can be a mixture thereof.

Examples of active oxygen compound include peroxygen compounds, peroxygen compound adducts, hydrogen peroxide, hydrogen peroxide liberating or generating compounds, and inorganic and organic peroxyacids. Many active oxygen compounds are peroxygen compounds, including for example hydrogen peroxide, group 1 (IA) active oxygen compounds (e.g., sodium peroxide), group 2 (IIA) active oxygen compounds (e.g., magnesium peroxide), group 12 (JIB) active oxygen compounds (e.g., zinc peroxide), group 13 (IIIA) active oxygen compounds (e.g., perborates), group 14 (WA) active oxygen compounds (e.g., persilicates and peroxycarbonates), group 15 (VA) active oxygen compounds (e.g., perphosphates), group 16 (VIA) active oxygen compounds (e.g., peroxysulfuric acids and their salts), group 17 (VITA) active oxygen compounds (e.g., sodium periodate), and transition metal peroxides. Any of a variety of hydrogen peroxide and/or hydrogen peroxide adducts are suitable for use in the present invention.

Sodium percarbonate ($2Na_2CO_3 \cdot 3H_2O_2$) is a preferred active oxygen compound for the stabilized solid activated bleach compositions. Percarbonate is an alternative to solid peroxide for use in solid detergent formulations. Sodium percarbonate is commercially-available in the form of coated granulates to provide enhanced stability.

Active oxygen compounds, including organic active oxygen compounds may also include peroxycarboxylic acids, such as a mono- or di-peroxycarboxylic acid, an alkali metal salt including these types of compounds, or an adduct of such a compound. Similarly, sulfoperoxycarboxylic acid, sulfonated peracid, or sulfonated peroxycarboxylic acid each refer synonymously to the peroxycarboxylic acid form of a sulfonated carboxylic acid and may be employed as active oxygen compounds. Peracid, peroxyacid, percarboxylic acid and peroxycarboxylic acid each refer synonymously to acids having the general formula $R(CO_3H)_n$. The R group can be saturated or unsaturated as well as substituted or unsubstituted. As described herein, R is an alkyl, arylalkyl, cycloalkyl, aromatic, heterocyclic, or ester group, such as an alkyl ester group. N is one, two, or three, and named by prefixing the parent acid with peroxy. Ester groups are defined as R groups including organic moieties (such as those listed above for R) and ester moieties. Exemplary ester groups include aliphatic ester groups, such as $R_1OC(O)_2$, where each of $R_1$ and $R_2$ can be aliphatic, preferably alkyl, groups described above for R. Preferably $R_1$ and $R_2$ are each independently small alkyl groups, such as alkyl groups with 1 to 5 carbon atoms.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups). Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Exemplary peroxycarboxylic acids for use with the present invention include, but are not limited to, peracetic acid, peroctanoic acid, a persulphate, a perborate, or a percarbonate. In preferred embodiments, the active oxygen use solution includes hydrogen peroxide, percarbonate and/or peracetic acid.

In some embodiments, the active oxygen source includes more than one active oxygen source. For example, combinations of active oxygen sources for use with the methods of the present invention can include, but are not limited to, peroxide/peracid combinations, percarbonate/peroxide, percarbonate/peracid, or peracid/peracid combinations, and combinations thereof.

The amount of active oxygen source in the active oxygen use solution is dependent on a variety of factors including, for example, the type of surface to be cleaned, and the amount and type of soil present on the surface. In aspects of the invention, the active oxygen source has a concentration in the stabilized solid activated bleach compositions from about 1 wt-% to about 75 wt-%, 10 wt-% to about 75 wt-%, from about 10 wt-% to about 50 wt-%, from about 20 wt-% to about 50 wt-%, or from about 25 wt-% to about 50 wt-%.

Sequestrant System

The stabilized solid activated bleach compositions according to the invention include a sequestrant system. Suitable sequestrants include for example, a phosphonate sequestrant. Phosphonates include, for example, pyrophosphates, polyphosphates, condensed phosphates, phosphonates, phosphonic acids, and the like. Additionally dipicolinic acid and other aminocarboxylate sequestrants are also suitable for use in the sequestrant systems. In an aspect, the dicarboxylates functionality is particularly well suited for the aminocarboxylate sequestrants. Mixtures thereof are further suitable for the sequestrant systems.

Phosphonates, including phosphonic acid, are preferred for use as sequestrants in the stabilized solid activated bleach compositions as they beneficially provide stability for the solid block compositions having a wet interface during dispensing, including multi-dispensing formulations. Examples of condensed phosphates include sodium and potassium orthophosphate, sodium and potassium pyrophosphate, sodium tripolyphosphate, sodium hexametaphosphate, and the like. The composition may include a phosphonate such as 1-hydroxyethane-1,1-diphosphonic acid $CH_3C(OH)[PO(OH)_2]_2$(HEDP); amino tri(methylenephosphonic acid) $N[CH_2PO(OH)_2]_3$; aminotri(methylenephosphonate), sodium salt $(NaO)(HO)P(OCH_2N[CH_2PO(ONa)_2]_2)$; 2-hydroxyethyliminobis(methylenephosphonic acid) $HOCH_2CH_2N[CH_2PO(OH)_2]_2$; diethylenetriaminepenta(methylenephosphonic acid) $(HO)_2POCH_2N[CH_2CH_2N[CH_2PO(OH)_2]_2]_2$; diethylenetriaminepenta(methylenephosphonate), sodium salt $C_9H_{(28-x)}N_3Na_xO_{15}P_5$ (x=7); hexamethylenediamine(tetramethylenephosphonate), potassium salt $C_{10}H_{(28-x)}N_2K_xO_{12}P_4$ (x=6); bis(hexamethylene)triamine(pentamethylenephosphonic acid) $(HO_2)POCH_2N[(CH_2)_6N[CH_2PO(OH)_2]_2]_2$; and phosphorus acid $H_3PO_3$.

An example of a commercially-available phosphonate sequestrant is Dequest 2016D, tetrasodium hydroxyethylidene bis-phosphonic acid (available from ThermoPhos). In the event a phosphonate sequestrants is employed for dispensing stability benefits, the stabilized solid activated bleach compositions are not formulated as phosphate-free compositions.

In aspects of the invention, the sequestrant has a concentration in the stabilized solid activated bleach compositions from about 0.01 wt-% to about 25 wt-%, 0.1 wt-% to about 20 wt-%, from about 0.5 wt-% to about 10 wt-%, or from about 0.5 wt-% to about 5 wt-%.

Binding System

The stabilized solid activated bleach compositions according to the invention include a binding system providing shelf stability and other benefits. In an aspect the binding system comprises, consists of and/or consists essentially of an anionic surfactant and a cellulose component. Without wishing to be bound by theory or a particular mechanism of action, the binding system prevents the bleach activating agent from reacting with the active oxygen source in the compositions which results in a maintained oxygen stability within the solid formulations. The binding systems maintain the oxygen stability through use of anhydrous binding agents, including for example spray dried surfactants and/or cellulose components.

In aspects of the invention, the binding system has a concentration in the stabilized solid activated bleach compositions from about 0.1 wt-% to about 25 wt-%, 1 wt-% to about 20 wt-%, from about 1 wt-% to about 15 wt-%, or from about 1 wt-% to about 10 wt-%.

Anionic Surfactant

The binding system of the stabilized solid activated bleach compositions according to the invention includes at least one anionic surfactant. In some embodiments more than one anionic surfactant may be employed in the binding system. Anionic surfactants are surface active substances having a negative charge on the hydrophobe or have a hydrophobic section that carries no charge unless the pH is elevated to neutrality or above (e.g. carboxylic acids). Carboxylate, sulfonate, sulfate, and phosphate are the polar (hydrophilic) solubilizing groups found in anionic surfactants. Of the cations (counter ions) associated with these polar groups, sodium, lithium, and potassium impart water solubility; ammonium and substituted ammonium ions provide both water and oil solubility; and, calcium, barium, and magnesium promote oil solubility.

In a preferred aspect, the anionic surfactant(s) are either not combined with any nonionic surfactants or combined with amounts of nonionic surfactant(s) which do not interfere with the stability of the solid compositions. In an aspect where a minor amount of nonionic surfactant not disrupting the stability of the solid composition is included, nonionic surfactant(s) may comprise no more than 5 wt-%, preferably no more than 2 wt-%, more preferably no more than 1 wt-%, and most preferably no more than 0.5 wt-%. Without being limited to a particular theory and/or mechanism of action, the nonionic surfactants having free alcohol groups interfere with the binding system maintaining oxygen stability in the solid compositions. Instead, anionic surfactants are employed and beneficially provide sulfonate/sulfate capping which provides sufficient binding to maintain oxygen stability in the solid compositions according to the invention.

The majority of large volume commercial anionic surfactants can be subdivided into five major chemical classes and additional sub-groups known to those of skill in the art and described in "Surfactant Encyclopedia," Cosmetics & Toiletries, Vol. 104 (2) 71-86 (1989). Further examples of suitable anionic surfactants are given in "Surface Active Agents and Detergents" (Vol. I and II by Schwartz, Perry and Berch). A variety of such surfactants are also generally disclosed in, for example, U.S. Pat. No. 3,929,678. The disclosures of the above references relating to anionic surfactants are incorporated herein by reference.

Anionic surfactants suitable for use in the present compositions include organic sulfonates, organic sulfates, organic phosphates, and organic carboxylates. In particular, linear alkyl aryl sulfonates, alkylarylcarboxylates and akylarylphosphates are suitable anionic surfactants. Exemplary anionic sulfate surfactants include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, sulfonated fatty acids, such as sulfonated oleic acid, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkyl aryl ethoxy carboxylates of the following formula:

$$R—O—(CH_2CH_2O)_n(CH_2)_m—CO_2X \qquad (3)$$

in which R is a $C_8$ to $C_{22}$ alkyl group or

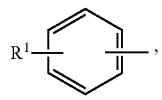

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

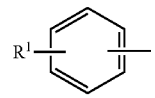

and $R^1$ is a $C_6$-$C_{12}$ alkyl group. In still yet other embodiments, $R^1$ is a $C_9$ alkyl group, n is 10 and m is 1.

In some embodiments, the anionic surfactant selected is a linear alkyl benzene sulfonate, an alcohol sulfate and derivatives and mixtures thereof. In some embodiments, a dodecylbenzene sulfonic acid (DDBSA) or linear alkylbenzene sulfonate (LAS) are selected for use with the compositions and methods of the present invention. The linear alkyl benzene sulfonates are preferably employed in the acid form to provide a viscous binding agent for the binding system. In the event a salt form of an anionic surfactant is employed the concentration required may be increased in comparison to the acid formulation.

In aspects of the invention, the anionic surfactant of the binding system has a concentration in the stabilized solid activated bleach compositions 0.1 wt-% to about 15 wt-%, 1 wt-% to about 10 wt-%, and preferably from about 2 wt-% to about 7.5 wt-%, or from about 2 wt-% to about 5 wt-%. In some aspects the ratio of the anionic surfactant to cellulose component in the binding system is in a ratio of from about 5:1 to about 1:5, from about 2:1 to about 1:2, or preferably about 1:1. It is to be understood that all values and ranges between these values and ranges are encompassed by the invention.

Cellulose

The binding system of the stabilized solid activated bleach compositions according to the invention include at least one cellulosic species or component, or a polymeric component (referred to herein as cellulose components). In some embodiments more than one cellulose component may be employed in the binding system. The cellulose components beneficially provides binding and dispensing aid to the solid compositions and further provides hydration.

Cellulose components may include substantially soluble cellulose thickeners and/or polymeric thickeners which increase viscosity. Examples of polymeric thickeners for the aqueous compositions of the invention include, but are not limited to: carboxylated vinyl polymers such as polyacrylic acids and sodium salts thereof, ethoxylated cellulose, polyacrylamide thickeners, cross-linked, xanthan compositions, sodium alginate and algin products, hydroxypropyl cellulose, hydroxyethyl cellulose, and other similar aqueous thickeners that have some substantial proportion of water solubility. In a preferred embodiment, the cellulose for the binding system is sodium carboxymethycellulose.

Carboxymethyl cellulose (CMC) is a carboxymethyl derivative of cellulose formed by the reaction of cellulose with alkali and chloroacetic acid. As a result of the reaction, carboxymethyl groups are bound to some of the hydroxyl groups of the glucopyranose units that make up the backbone of cellulose. The degree of substitution of carboxymethyl varies from about 0.6 to 0.95 per glucopyranose unit. Carboxymethyl cellulose is available in various molecular weights. Low molecular weight carboxymethyl cellulose has a Mw of about 90,000 and a 2% solution thereof will have a viscosity of about 1.1 cP at 25.degree. C. Medium weight carboxymethyl cellulose has a Mw of about 250,000. High molecular weight carboxymethyl cellulose has a Mw of about 700,000 and a 2% solution will have a viscosity of about 12 cP at 25° C. For the purpose of the present invention, any molecular weight CMC may be used, even mixtures of different weights. For example, from 25/75 to 75/25 carboxymethyl cellulose, preferably from 30/70 to 70/30 and most preferably about 35/65 medium/high molecular weight sodium carboxymethyl cellulose. Also any degree of substitution may be.

In aspects of the invention, the cellulose component of the binding system has a concentration in the stabilized solid activated bleach compositions 0.1 wt-% to about 15 wt-%, 1 wt-% to about 10 wt-%, from about 1 wt-% to about 7.5 wt-%, or from about 1 wt-% to about 5 wt-%.

Alkaline Solidification Matrix

The stabilized solid activated bleach compositions of the present invention include at least one alkaline solidification matrix. In some aspects, the alkaline solidification matrix function as a hydratable salt to form the solid compositions. In some aspects, the hydratable salt can be referred to as substantially anhydrous or anhydrous. As one skilled in the art will ascertain from the disclosure herein, there may also be included with the alkaline solidification matrix in the solid detergent composition water of hydration to hydrate the alkaline solidification matrix. It should be understood that the reference to water includes both water of hydration and free water. However, according to the invention, the stabilized solid activated bleach compositions are water-free systems, including having water in the solid composition in an amount less than about 1% by weight, less than about 0.5% by weight, less than about 0.1% by weight, less than about 0.05% by weight, and most preferably free of water (i.e. dried).

In some aspects, the alkaline solidification matrix may include alkali metal carbonates and/or alkali metal silicates. Examples of suitable alkaline solidification matrix include but are not limited to: sodium carbonate, potassium carbonate, sodium silicate, potassium silicate, a mixture of alkali metal carbonates, a mixture of alkali metal silicates, and any mixtures of the same. In additional aspects, the alkaline solidification matrix may include alkali metal metasilicates, bicarbonates, sesquicarbonates, and mixtures thereof. In an aspect, the alkaline solidification matrix does not include any alkali metal hydroxides.

In an aspect, alkali metal carbonates are particularly well suited for use in the stabilized solid activated bleach compositions. Exemplary alkali metal carbonate compounds include but are not limited to synthetic light ash, natural light ash, dense ash and mono ash.

The alkaline solidification matrix largely controls the pH of the resulting solution when water is added to the detergent composition to form a use solution. In some aspects, the alkalinity source(s) provide a high alkaline detergent. In such aspects, the pH of the use solution is between approximately 8.5 and approximately 11.5. In some aspects, the pH of the use solution is between about 9 and about 11. In other aspects, the alkaline solidification matrix (e.g. sodium carbonate) provide a milder alkaline detergent, such as a pH greater than about 7; such as disclosed in U.S. Pat. No. 7,094,746, which is incorporated herein by reference in its entirety. Beneficially, the stabilized solid activated bleach compositions can be formulated into alkaline and/or highly alkaline compositions while still protecting the reactive materials.

In aspects of the invention the alkaline solidification matrix are included in the stabilized solid activated bleach compositions at a concentration of from about 10 wt-% to about 80 wt-%, from about 10 wt-% to about 70 wt-%, from about 15 wt-% to about 60 wt-%, or and from about 20 wt-% to about 40 wt-%. It is to be understood that all values and ranges between these values and ranges are encompassed by the invention.

Additional Functional Ingredients

The components of the stabilized solid activated bleach compositions can further be combined with various functional components. In some embodiments, the stabilized solid activated bleach compositions include the bleach activating agent, peroxygen source, alkaline solidification matrix, and binding system which make up a large amount, or even substantially all of the total weight of the stabilized solid activated bleach compositions. For example, in some embodiments few or no additional functional ingredients are disposed therein.

In other embodiments, additional functional ingredients may be included in the compositions. The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, as a broad variety of other functional ingredients may be used. For example, many of the functional materials discussed below relate to materials used in sanitizing and bleaching, specifically warewash and/or laundry applications. However, other embodiments may include functional ingredients for use in other applications.

In some embodiments, the compositions may include additional acidic components, surfactants, solvents, catalysts, defoaming agents, anti-redeposition agents, additional bleaching agents, additional surfactants for detergency, water conditioning polymers, solubility modifiers, dispersants, rinse aids, metal protecting agents, stabilizing agents, corrosion inhibitors, surface modification polymers, such as soil release polymers, additional bleach activators, whitening additives, such as optical brighteners or hueing agents, additional sequestrants, hardening agents, builders and/or chelating agents, enzymes, fragrances and/or dyes, rheology modifiers or thickeners, hydrotropes or couplers, buffers, solvents and the like.

Additional Acidic Components

In some embodiments, the compositions further include an additional acid. Any acid suitable for use in stabilizing the composition and/or treating a surface for a particular application of use can be used. For example, the compositions can further include organic acids (e.g., citric acid, lactic acid, acetic acid, hydroxyacetic acid, glutamic acid, glutaric acid, methane sulfonic acid, acid phosphonates (e.g., HEDP), and gluconic acid) and/or mineral acids (e.g., phosphoric acid, nitric acid, sulfuric acid). In some embodiments, the ideal additional acidic component provides good chelation, as well as improved shelf-life for the solid compositions.

The stabilized solid activated bleach compositions can include additional acidic components in amounts from about 0.01 to 50% by weight, preferably 0.1 to 25% by weight, preferably 0.5 to 10% by weight, and more preferably 1 to 5% by weight.

Chelants or Sequestrants

In some embodiments, the compositions include an additional chelant/sequestering agent. Suitable chelating/sequestering agents are, for example, citrate or citric acid, aminocarboxylic acid, aminocarboxylates and their derivatives, pyrophosphates, polyphosphates, ethylenediamene and ethylenetriamene derivatives, hydroxyacids, and mono-, di-, and tri-carboxylates and their corresponding acids, condensed phosphate, phosphonate, phosphonic acid and polyacrylates, aluminosilicates, nitroloacetates and their derivatives, and mixtures thereof. In general, a chelating agent is a molecule capable of coordinating (i.e., binding) the metal ions commonly found in natural water to prevent the metal ions from interfering with the action of the other detersive ingredients of a cleaning composition. In general, chelating/sequestering agents can generally be referred to as a type of builder. The chelating/sequestering agent may also function as a threshold agent when included in an effective amount.

In some embodiments, an organic chelating agent is used. Organic chelating agents include both polymeric and small molecule chelating agents. Organic small molecule chelating agents are typically organocarboxylate compounds or organophosphate chelating agents. Polymeric chelating agents commonly include polyanionic compositions such as polyacrylic acid compounds.

Suitable aminocarboxylic acids include, for example, methylglycinediacetic acid (MGDA), N-hydroxyethyliminodiacetic acid, nitrilotriacetic acid (NTA), ethylenediaminetetraacetic acid (EDTA), N-hydroxyethyl-ethylenediaminetriacetic acid (HEDTA), diethylenetriaminepentaacetic acid (DTPA), ethylenediaminetetraproprionic acid triethylenetetraaminehexaacetic acid (TTHA), and the respective alkali metal, ammonium and substituted ammonium salts thereof. Examples of condensed phosphates include sodium and potassium orthophosphate, sodium and potassium pyrophosphate, sodium tripolyphosphate, sodium hexametaphosphate, and the like.

The chelating/sequestering agent may also be a water conditioning polymer that can be used as a form of builder. Such suitable sequestrants include water soluble polycarboxylate polymers. Such homopolymeric and copolymeric chelating agents include polymeric compositions with pendant (—CO$_2$H) carboxylic acid groups and include polyacrylic acid, polymethacrylic acid, polymaleic acid, acrylic acid-methacrylic acid copolymers, acrylic-maleic copolymers, hydrolyzed polyacrylamide, hydrolyzed methacrylamide, hydrolyzed acrylamide-methacrylamide copolymers, hydrolyzed polyacrylonitrile, hydrolyzed polymethacrylonitrile, hydrolyzed acrylonitrile methacrylonitrile copolymers, or mixtures thereof. Water soluble salts or partial salts of these polymers or copolymers such as their respective alkali metal (for example, sodium or potassium) or ammonium salts can also be used. The weight average molecular weight of the polymers is from about 4000 to about 12,000. Preferred polymers include polyacrylic acid, the partial sodium salts of polyacrylic acid or sodium polyacrylate having an average molecular weight within the range of 4000 to 8000.

Exemplary water conditioning polymers include polycarboxylates. Exemplary polycarboxylates that can be used as water conditioning polymers include polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, and hydrolyzed acrylonitrile-methacrylonitrile copolymers.

The stabilized solid activated bleach compositions can include an additional chelating/sequestering agent in amounts from about 0.01 to 50% by weight, preferably 0.1 to 25% by weight, preferably 0.1 to 5% by weight, and more preferably 0.5 to 5% by weight.

Catalyst

The stabilized solid activated bleach compositions according to the invention may include at least one catalyst in addition to the bleach activating agent. The term "catalyst," as used herein, refers to an agent, such as transition metals, used to activate a source of oxygen, such as a percarbonate, providing improved bleaching activity and/or bubbling of a use solution to provide enhanced cleaning efficacy. In an aspect, catalysts are suitable for converting or decomposing active oxygen sources (i.e. oxidation) to generate catalytically enhanced bleaching species. In an aspect of the invention, the catalyst is readily degraded and therefore is in need of the coating using the polymeric matrix according to the invention. For example, Mn (II) or Mn (III) are readily oxidized to form Mn (IV) species (turning to MnO$_2$), in particular when combined with oxidants and/or in an alkaline environment.

In an aspect of the invention, the catalyst agent is metallic. In a further aspect, the catalyst agent can include various forms of metallic agents, including transition metals, including for example manganese. In some aspects, the catalyst agent includes at least once source of manganese. In some embodiments, the manganese source is derived from manganese metal, manganese oxides, colloidal manganese, inorganic or organic complexes of manganese, including manganese sulfate, manganese carbonate, manganese acetate, manganese lactate, manganese nitrate, manganese gluconate, or manganese chloride, or any of the salts of salt forming species with manganese. Exemplary manganese-gluconate complexes are described in EP0237111; manganese-bipyridylamine complexes are described in EP0392593; and manganese-polyol complexes are described in EP0443651, as peroxygen bleach catalysts. Commercially-available manganese catalysts are sold under the tradename Dragon (also known as Dragon's Blood or Dragon A350) (bis (octahydro-1,4,7-trimethyl-1H-1,4,7-triazonine-kN$^1$,kN$^4$, kN$^7$)-tri-μ-oxo-Di[manganese(1+)]sulfate tetrahydrate) or tradename Pegasus (Di[manganese(1+)], 1,2-bis(octahydro-4,7-dimethyl-1H-1,4,7-triazonine-1-yl-kN$^1$,kN$^4$,kN$^7$)-ethane-di-μ-oxo-μ-(ethanoato-kO,kO')-, di[chloride (1−)]), available from Catexel Ltd.

In an aspect, the catalyst agent is a manganese-based complex that is a mononuclear or dinuclear complex of a Mn(III) or Mn(IV) transition metal. In a further aspect, the catalyst agent contains at least one organic ligand containing at least three nitrogen atoms that coordinate with the manganese. An exemplary structure is 1,4,7-triazacyclononane (TACN), 1,4,7-trimethyl-1,4,7-triazacyclononane (Me-TACN), 1,5,9-triazacyclododecane, 1,5,9-trimethyl-1,5,9-triazacyclododecane (Me-TACD), 2-methyl-1,4,7-triazacyclononane (Me/TACN), 2-methyl-1,4,7-trimethyl-1,4,7-triazacyclononane (Me/Me-TACN), N,N',N''-(2-hyroxyethyl)1,4,7-triazacyclononane. In a preferred embodiment, the ratio of the manganese atoms to the nitrogen atoms is 1:3.

Catalysts can also contain from 0 to 6 coordinating or bridging groups per manganese atom. When the manganese based catalyst is a mononuclear complex, coordinating groups are for example selected from —OMe, —O—CH$_2$—CH$_3$, or —O—CH$_2$—CH$_2$—CH$_3$. When the manganese based catalyst is a dinuclear complex, bridging groups may be selected, among others, from —O—, —O—O—, or —O—CH(Me)-O—. The catalyst can also contain one or more monovalent or multivalent counter ions leading to a charge neutrality. The number of such monovalent or multivalent counter ions will depend on the charge of the manganese complex which can be 0 or positive. The type of the counter ions needed for the charge neutrality of the complex is not critical and the counter ions may be selected for example from halides such as chlorides, bromides and iodides, pseudohalides, sulphates, nitrates, methylsulfates, phosphates, acetates, perchlorates, hexafluorophosphates, or tetrafluoro-borates.

The catalysts suitable for use according to the invention may be defined according the following formula: $[(L_pM_n)_nX_r]Y_s$, wherein each L independently is an organic ligand containing at least three nitrogen atoms and/or at least two carboxyl groups that coordinate with the Mn metal; each X independently is a coordinating or bridging group selected from the group consisting of $H_2O$, $OH^-$, $SH^-$, $HO_2^-$, $O^{2-}$, $O_2^{2-}$, $S^{2-}$, $F^-$, $Cl^-$, $Br^-$, $I^-$, $NO_3^-$, $NO_2^-$, $SO_4^{2-}$, $SO_3^{2-}$, $PO_4^{3-}$, $N_3^-$, $CN^-$, $NR_3$, $NCS^-$, $RCN$, $RS^-$, $RCO_2^-$, $RO^-$, and

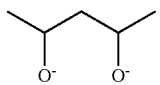

with R being hydrogen or a $C_1$ to $C_6$ alkyl group; p is an integer from 1 to 4; q is an integer from 1 to 2; r is an integer from 0 to 6; Y is a counter ion; and s is the number of counter ions.

The catalysts suitable for use according to the invention may also be defined according the following formula for a dinuclear manganese complex:

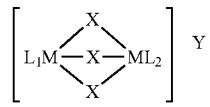

wherein M is a Mn metal; $L_1$ and $L_2$ can either be separate ligands or where $L_1$ and $L_2$ can combine to be a single molecule. Among the coordinating or bridging groups, the groups $O^{2-}$, $O_2^{2-}$, $CH_3O-$, $CH_3CO_2^-$,

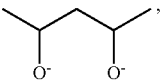

or Cl— are particularly preferred. In some aspects, the ligands are selected from the group consisting triazacyclononane, triazacyclononane derivatives, Schiff-base containing ligands, polypyridineamine ligands, pentadentate nitrogen-donor ligands, bispidon-type ligands, and macrocyclic tetraamidate ligands. Examples for those classes of ligands are described by R. Hage and A Lienke (Hage, Ronald; Lienke, Achim. Applications of Transition-Metal Catalysts to Textile and Wood-Pulp Bleaching. Angewandte Chemie International Edition, 2005, 45. Jg., Nr. 2, pp. 206-222), which is incorporated herein by reference in its entirety. Another group of preferred ligands are dicarboxylates, in particular oxalate.

Additional disclosure of metal complexes for catalysts is provided for example, in U.S. patent application Ser. No. 14/303,706, and U.S. Pat. Nos. 5,227,084, 5,194,416, 4,728,455, 4,478,733, and 4,430,243, and European Patent Nos. 693,550, 549,271, 549,272, 544,519, 544,490, 544,440, 509, 787, 458,397 and 458,398, each of which is herein incorporated by reference in its entirety.

In aspects of the invention, a catalyst may be included in the stabilized solid activated bleach compositions in amounts ranging from about 0 wt-% to about 10 wt-%, from about 0.001 wt-% to about 5 wt-%, or from about 0.01 wt-% to about 1 wt-%.

Solvents

In some embodiments, the stabilized solid activated bleach compositions include a solvent to combine the bleaching activating agent, peroxygen source and/or binding system into a mixture before drying and/or solidifying. In preferred aspects, the solvent is substantially-free of water or preferably water-free. In some aspects, the solvent is a polar or non-polar solvent. According to the invention, the solvents must be suitable for the drying or evaporation according to the methods of making the stabilized solid activated bleach compositions. Representative polar solvents include for example, alcohols (including straight chain or branched aliphatic alcohols, such as methanol), glycols and derivatives, and the like. Representative non-polar solvents include for example, aliphatics, aromatics, and the like.

The stabilized solid activated bleach compositions can include 0 to 50% by weight, preferably 0.001 to 25% by weight, more preferably 0.01 to 5% by weight of a solvent.

Surfactants

In some embodiments, the stabilized solid activated bleach compositions of the present invention include a surfactant or surfactant system in addition to the anionic surfactant(s) of the binding system. A variety of surfactants can be used in sanitizing and/or bleaching applications, including, but not limited to: anionic, cationic, amphoteric, zwitterionic, and nonionic surfactants.

Exemplary surfactants that can be used are commercially available from a number of sources. For a discussion of surfactants, see for example, Kirk-Othmer, Encyclopedia of Chemical Technology, Third Edition, volume 8, pages 900-912, "Surface Active Agents and Detergents," Vol. I and II by Schwartz, Perry and Berch, each of which are herein incorporated by reference in its entirety.

Additional surfactants may be selected based on particular applications of use. For example, warewash applications may employ additional anionic surfactants or other low-foaming surfactants. Higher foaming applications may employ foaming surfactants, such as linear alkyl benzene sulfonates.

Non-limiting examples of anionic surfactants useful in the stabilized solid activated bleach compositions include, but are not limited to: carboxylates such as alkylcarboxylates and polyalkoxycarboxylates, alcohol ethoxylate carboxylates, nonylphenol ethoxylate carboxylates; sulfonates such as alkylsulfonates, alkylbenzenesulfonates, alkylarylsulfonates, sulfonated fatty acid esters; sulfates such as sulfated alcohols, sulfated alcohol ethoxylates, sulfated alkylphenols, alkylsulfates, sulfosuccinates, and alkylether sulfates. Exemplary anionic surfactants include, but are not limited to: sodium alkylarylsulfonate, alpha-olefinsulfonate, and fatty alcohol sulfates.

Non-limiting examples of cationic surfactants that can be used in the stabilized solid activated bleach compositions include, but are not limited to: amines such as primary, secondary and tertiary monoamines with C18 alkyl or alkenyl chains, ethoxylated alkylamines, alkoxylates of ethylenediamine, imidazoles such as a 1-(2-hydroxyethyl)-2-imidazoline, a 2-alkyl-1-(2-hydroxyethyl)-2-imidazoline, and the like; and quaternary ammonium salts, as for example, alkylquaternary ammonium chloride surfactants such as n-alkyl(C12-C18)dimethylbenzyl ammonium chloride, n-tetradecyldimethylbenzylammonium chloride mono-hydrate, and a naphthylene-substituted quaternary ammonium chloride such as dimethyl-1-naphthylmethylammonium chloride. The cationic surfactant can be used to provide sanitizing properties.

Non-limiting examples of nonionic surfactants useful in the detergent composition include, but are not limited to, those having a polyalkylene oxide polymer as a portion of the surfactant molecule. Such nonionic surfactants include, but are not limited to: chlorine-, benzyl-, methyl-, ethyl-, propyl-, butyl- and other like alkyl-capped polyethylene glycol ethers of fatty alcohols; polyalkylene oxide free nonionics such as alkyl polyglycosides; sorbitan and sucrose esters and their ethoxylates; alkoxylated amines such as alkoxylated ethylene diamine; alcohol alkoxylates such as alcohol ethoxylate propoxylates, alcohol propoxylates, alcohol propoxylate ethoxylate propoxylates, alcohol ethoxylate butoxylates; nonylphenol ethoxylate, polyoxyethylene glycol ether; carboxylic acid esters such as glycerol esters, polyoxyethylene esters, ethoxylated and glycol esters of fatty acids; carboxylic amides such as diethanolamine condensates, monoalkanolamine condensates, polyoxyethylene fatty acid amides; and polyalkylene oxide block copolymers.

Non-limiting examples of amphoteric surfactants useful in the stabilized solid activated bleach compositions include, but are not limited to: derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. In particular, amphoteric surfactants are subdivided into two major classes: acyl/dialkyl ethylenediamine derivatives (e.g. 2-alkyl hydroxyethyl imidazoline derivatives) and their salts; and N-alkylamino acids and their salts.

Non-limiting examples of zwitterionic surfactants that can be used in the stabilized solid activated bleach compositions include, but are not limited to: betaines, imidazolines, and propionates.

When the stabilized solid activated bleach compositions include an additional surfactant or surfactant system for sanitizing and/or bleaching or other cleaning benefits, they may be included in an amount effective to provide a desired level of cleaning, sanitizing and/or bleaching. In some embodiments, the compositions of the present invention include about 0.01 wt-% to about 50 wt-% of an additional surfactant or surfactant system. In other embodiments the compositions of the present invention include about 1 wt-% to about 50 wt-% of an additional surfactant or surfactant system. In still yet other embodiments, the compositions of the present invention include about 5 wt-% to about 40 wt-% of an additional surfactant or surfactant system, or from about 5 wt-% to about 25 wt-% of an additional surfactant or surfactant system.

Methods of Making

The stabilized solid activated bleach compositions are made suitable to provide stability such that reactive components in the compositions do not react with each other until a point of dilution and/or use. In some aspects, the order of introducing the components to form the solid are non-limiting as there is minimal and/or no water introduced into the solid compositions. However, in some aspects, the stabilized solid activated bleach compositions are made by first combining the binding system according to the invention, the peroxygen source and then the bleach activator in the weight ratios disclosed according to the embodiments of the invention to minimize any damage to the coated granules which may be employed. In a further aspect, the binding system and peroxygen source are mixed to ensure homogenous distribution prior to adding the bleach activator. Regardless of the order of addition of components, the compositions are unable to be formed by a traditional ash-based hydration due to any water in the composition causing a reduction in available oxygen stability.

Beneficially, according to the invention the solidification mechanism to make the stabilized solid activated bleach compositions generates a solid and prevents the reaction of the active oxygen source and bleach activating agent due to the binding system employed therein. The solid composition remains unreacted until a point of use, e.g. dilution.

In a pressed solid process, a flowable solid, such as granular solids or other particle solids including binding agents are combined under pressure. In a pressed solid process, flowable solids of the compositions are placed into a form (e.g., a mold or container). The method can include gently pressing the flowable solid in the form to produce the solid cleaning composition.

The method can further include a curing step to produce the solid cleaning composition. As referred to herein, an uncured composition including the flowable solid is compressed to provide sufficient surface contact between particles making up the flowable solid that the uncured composition will solidify into a stable solid cleaning composition. A sufficient quantity of particles (e.g. granules) in contact with one another provides binding of particles to one another effective for making a stable solid composition. Inclusion of a curing step may include allowing the pressed solid to solidify for a period of time, such as a few hours, or about 1 day (or longer). In additional aspects, the methods could include vibrating the flowable solid in the form or mold, such as the methods disclosed in U.S. Pat. No. 8,889,048, which is herein incorporated by reference in its entirety.

The use of pressed solids provide numerous benefits over conventional solid block or tablet compositions requiring high pressure in a tablet press, or casting requiring the melting of a composition consuming significant amounts of energy, and/or by extrusion requiring expensive equipment and advanced technical know-how. Pressed solids overcome such various limitations of other solid formulations for which there is a need for making solid cleaning compositions. Moreover, pressed solid compositions retain its shape under conditions in which the composition may be stored or handled.

In an aspect, the methods of making reduce or eliminate water from the system prior to solidification. Preferably, the compositions are formed using components in an anhydrous form. In an aspect, compositions have a water content of less than about 1% by weight, less than about 0.5% by weight, less than about 0.1% by weight, less than about 0.05% by weight, and most preferably free of water (i.e. dried). In an aspect, the dried composition may be in the form of granules. Therefore, pressed solid formulations are preferred due to the removal of water from the compositions and ash hydration is not employed as a solidification mechanism.

The particulate product of the invention can be in the form of granules and/or flakes, but is preferably presented in the form of regular small granules. Thereafter, the granules are used to form solids. In a preferred aspect a pressed solid is formed. The solidification process may last from a few seconds to several hours, depending on factors including, but not limited to: the size of the formed or cast composition, the ingredients of the composition, and the temperature of the composition.

The solid detergent compositions may be formed using a batch or continuous mixing system. In an exemplary embodiment, a single- or twin-screw extruder is used to combine and mix one or more cleaning agents at high shear to form a homogeneous mixture. In some embodiments, the processing temperature is at or below the melting temperature of the components. The processed mixture may be dispensed from the mixer by forming, casting or other suitable means, whereupon the detergent composition hardens to a solid form. The structure of the matrix may be characterized according to its hardness, melting point, material distribution, and other like properties according to known methods in the art. Generally, a solid detergent composition processed according to the method of the invention is substantially homogeneous with regard to the distribution of ingredients throughout its mass and is dimensionally stable.

By the term "solid," it is meant that the hardened composition will not flow and will substantially retain its shape under moderate stress or pressure or mere gravity. The degree of hardness of the solid cast composition may range from that of a fused solid product which is relatively dense and hard, for example, like concrete, to a consistency characterized as being a hardened paste. In addition, the term "solid" refers to the state of the detergent composition under the expected conditions of storage and use of the solid detergent composition. In general, it is expected that the detergent composition will remain in solid form when exposed to temperatures of up to approximately 100° F. and particularly up to approximately 120° F.

The resulting solid detergent composition may take forms including, but not limited to: a pressed solid; a cast solid product; an extruded, molded or formed solid pellet, block, tablet, powder, granule, flake or the like. In certain embodiments, the solid detergent composition is provided in the form of a unit dose. A unit dose refers to a solid detergent composition unit sized so that the entire unit is used during a single washing cycle. When the solid detergent composition is provided as a unit dose, it is typically provided as a cast solid, an extruded pellet, or a tablet having a size of between approximately 1 gram and approximately 50 grams.

In other embodiments, the solid detergent composition is provided in the form of a multiple-use solid, such as a block or a plurality of pellets, and can be repeatedly used to generate aqueous detergent compositions for multiple washing cycles. In certain embodiments, the solid detergent composition is provided as a cast solid, an extruded block, or a tablet having a mass of between approximately 5 grams and approximately 15 kilograms. The stabilized formulations according to the invention providing for multiple dispensing of the bleaching compositions allow dispensing of the composition for a period of time ranging from at least a few hours to about 2 weeks, from about 12 hours to about 2 weeks, from about 1 day to about 14 days, while maintaining the stability and efficacy of the bleaching compositions.

Methods of Use

In some aspects, the stabilized solid activated bleach compositions are suitable for use in various applications that requires shelf stability or protection of a bleach activator in a solid composition containing an active oxygen source. Such uses may be referred to generally as those requiring an activated bleaching system. Without being limited according to the applications of use of the invention, the stabilized solid activated bleach compositions are particularly suitable for the protection of a peroxygen species in the presence of oxidation catalysts or bleach activators in bleaching systems, such as for laundry and warewashing. In particular, the bleaching systems may include warewash detergents, coffee and/or tea destainers, clean-in-place (CIP) applications employing peroxygen activation catalysts for peroxide or peracid cleaners, hard surfacing cleaning, surgical instrument cleaning and the like, laundry applications, and the like.

In a further aspect however, the stabilized solid activated bleach compositions are suitable for protection of peroxygen species in the presence of bleaching activators in wastewater treatment, epoxidation reactions, and many other applications. In such applications there is a need for the removal of microbes (e.g. wastewater treatment) from wastewater which is often rich in malodorous compounds of reduced sulfur, nitrogen, phosphorous and the like. In such aspects, detergent compositions containing a strong oxidant are employed to convert these compounds efficiently to their odor free derivatives e.g. the sulfates, phosphates and amine oxides. These same properties are very useful in the treatment of other water sources, including industrial applications (e.g. treatment of slick water and other applications customary in oil and/or gas drilling) where the property of bleaching is also of great utility.

In still further aspects, the stabilized solid activated bleach compositions are suitable for protection of bleaching activators in pulp and paper bleaching. As referred to herein, pulp and paper bleaching may be employed in the "papermaking process," referring to methods of making paper products from pulp generally comprising forming an aqueous cellulosic papermaking furnish, draining the furnish to form a sheet and drying, the sheet. The steps of forming the papermaking furnish, draining, and drying may be carried out in any conventional manner generally known to those skilled in the art. The pulp may be any either or both of virgin pulp and recycled pulp.

In some aspects, the stabilized solid activated bleach compositions are preferably for use in an automatic washing detergent formulation e.g. such as a dishwasher detergent or a laundry detergent.

In some aspects, the stabilized solid activated bleach compositions are contacted by a diluent, such as water to generate a concentrate and/or use solution for the various applications of use. According to aspects of the multi-dispense solid compositions the formulation remains stable during use where water or other diluent contacts the solid (e.g. water is sprayed at a portion of the solid to cause reaction upon dilution of a portion of the solid). In an aspect, the solid composition remains stable for several hours to several weeks, from about 1 day to about 2 weeks. Beneficially, the solid composition delivers a desired amount of active oxygen sanitizing agent (e.g. peracetic acid) during dispensing to obtain the desired bleaching, antimicrobial and/or sanitizing effect, without causing the reaction of the remainder of the reactive components in the solid formulation as a result of the sequestrant system incorporated therein with the binding system and reactive components.

The solid compositions will react upon dilution (e.g. sodium percarbonate and TAED) to form a bleaching agent (e.g. peracetic acid). The stabilized solid activated bleach compositions can include concentrate compositions or can be diluted to form use compositions. In general, a concentrate refers to a composition that is intended to be diluted with water to provide a use solution that contacts an object to provide the desired cleaning, rinsing, or the like. The detergent composition that contacts the articles to be washed can be referred to as the use composition. The use solution can include additional functional ingredients at a level suitable for cleaning, bleaching, or the like.

A use solution may be prepared from the concentrate by diluting the concentrate with water at a dilution ratio that provides a use solution having desired detersive properties. The water that is used to dilute the concentrate to form the use composition can be referred to as water of dilution or a diluent, and can vary from one location to another. The typical dilution factor is between approximately 1 and approximately 10,000 but will depend on factors including water hardness, the amount of soil to be removed and the like. In one embodiment, the concentrate is diluted at a ratio of between about 1:10 and about 1:1000 concentrate to water. Particularly, the concentrate is diluted at a ratio of between about 1:100 and about 1:5000 concentrate to water.

In some aspects, the concentrate compositions according to the invention are provided in the dilution range of about 0.01 g/L to about 10 g/L, from about 0.1 g/L to 10 g/L, from about 0.1 g/L to 5 g/L (e.g. sanitizing for equipment, such as a laundry machine), from about 0.2 g/L to 5 g/L, from about 0.5 g/L to 5 g/L (e.g. laundry applications), from about 0.5 g/L to 4 g/L, which will depend upon the dosing required for a particular application of use (e.g. warewash detergent, laundry detergent, or the like).

In some aspects, the present invention provides methods for removing soils from a surface, e.g., a hard surface, and/or bleaching a surface. In some embodiments, the method comprises applying a use solution of the detergent composition (e.g. contacting) to the surface, and removing the composition from the surface after an amount of time sufficient to facilitate soil removal and/or bleaching. The contacting step can last for any suitable time. In some embodiments, the contacting step lasts for at least 10 seconds, 20 seconds, 30 seconds, 40 seconds, 50 seconds, 1 minute, 10 minutes, 30 minutes, 1 hour, 2 hours, 4 hours, 8 hours, 16 hours, 1 day, 3 days, 1 week, or longer. The detergent composition can be applied to the surface (or target for soil removal and/or bleaching) in any suitable manner. In some embodiments, the detergent composition is applied by means of a spray, a foam, or the like.

The methods can be used to achieve any suitable removal of soil (e.g. cleaning), sanitizing, disinfecting, bleaching and/or reduction of the microbial population in and/or on the surface or target. In some embodiments, the methods can be used to reduce the microbial population by at least one log 10. In other embodiments, the present methods can be used to reduce the microbial population in and/or on the target or the treated target composition by at least two log 10. In still other embodiments, the present methods can be used to reduce the microbial population in and/or on the target or the treated target composition by at least three log 10.

In some embodiments, the method further comprises rinsing the surface. In some embodiments, the method further comprises generating a bubbling effect of the detergent compositions containing the active oxygen source and catalyst (and/or an active oxygen source combined with the detergent composition containing the catalyst). In some embodiments, the method further comprises a mechanical application of force, agitation and/or pressure to assist in removing the soils and/or bleaching the surface.

The methods of the present invention can be used to remove a variety of soils from a variety of surfaces and/or bleaching a variety of surfaces. For example, surfaces suitable for cleaning using the methods of the present invention include, but are not limited to, walls, floors, ware, dishes, flatware, pots and pans, heat exchange coils, ovens, fryers, smoke houses, sewer drain lines, and the like.

In some embodiments, the methods of the present invention are followed by only a rinse step. In other embodiments, the methods of the present invention are followed by a conventional CIP method suitable for the surface to be cleaned. In still yet other embodiments, the methods of the present invention are followed by a CIP method such as those described in U.S. Pat. Nos. 8,398,781 and 8,114,222 entitled "Methods for Cleaning Industrial Equipment with Pre-treatment," both of which are hereby incorporated by reference in their entirety.

Beneficially, according to the various aspects, the methods protect peroxygen (or other active oxygen sources) from the bleach activators formulated within the stabilized solid activated bleach compositions prior to a point of use. In other aspects, the methods protect the bleach activators formulated within the stabilized solid activated bleach compositions from high alkalinity from the solid compositions prior to a point of use.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The following materials were employed in the Examples for evaluation of exemplary embodiments of the stabilized solid activated bleach compositions.

Active Oxygen Source: Sodium Percarbonate (Sodium carbonate peroxyhydrate).

Bleach Activating Agents: Tetraacetylethylenediamine (TAED).

Alkaline Solicitation Matrix: Dense soda ash (sodium carbonate).

Sequestrant Systems: Hydroxyethylidene diphosphonic acid, dipicolinic acid

Binding Systems: Alkylbenzene sulfonic acid, linear alkylbenzene sulfonate, sodium CMC, Additional Functional Ingredients: Sodium chloride, citric acid Example 1

Various formulations of a stabilized solid activated bleach composition containing both an active oxygen source and a bleach activating agent were evaluated to determine the efficacy of various binding agents/systems for maintaining solid stability and a sequestrant system for improving dispensing stability. The formulations were made into 3 lb. multidispense blocks of pressed solids containing sodium percarbonate and TAED in addition to binding systems and sequestrant systems. The amount of available oxygen and peracetic acid was evaluated as it is indicative of the dispensing stability of the solid compositions to ensure the bleach activating agent and active oxygen source are not prematurely reacting and/or degrading in the solid formulations during extended dispensing as would be commercially applicable for multi-dispensing formulations.

The combination of the sequestrant systems and binding agents in the solid compositions set forth in the formulations of Table 2 were evaluated for ability to provide stability improvements. The formulations shown in Table 2 were used to produce pressed solid compositions employing percarbonate formulations with commercially-available tetraacetylethylenediamine as the bleach activating agent.

TABLE 2

| Raw Material | Evaluated Formulations | | |
|---|---|---|---|
| | 1 | 2 | 3 |
| Dense Soda Ash | 26 | 25.5 | 25.4 |
| Sodium Chloride | 5 | 5 | 5 |
| Citric Acid | 5 | 5 | 5 |
| Sodium carboxymethyl cellulose | 2 | 2 | 2 |
| Hydroxyethylidene diphosphonic acid | | 0.5 | 0.5 |
| Dipicolinic Acid | | | 0.1 |
| Sodium Percarbonate | 40 | 40 | 40 |
| Alkylbenzene Sulfonic Acid | 2 | 2 | 2 |
| Tetraacetylethylenediamine | 20 | 20 | 20 |

Formulation 1 represents a control formulation as no sequestrant system is included. The shelf stability of Formulation 1 has been established to demonstrate the use of a binding system in combination with the active oxygen and bleach activating agent according to the invention and is disclosed and illustrated in U.S. patent application Ser. No. 14/678,081, entitled Enhanced Peroxygen Stability using Anionic Surfactant in TAED-Containing Peroxygen Solid, which is herein incorporated by reference including, without limitation, the examples demonstrating shelf stability.

The solid formulations were evaluated over hourly dispensing measurements and daily dispensing measurements to determine the percentage of available oxygen and peracetic acid over the time spans. The measurement of available peracids and oxygen is reflective of the survival of these components during dispensing where there is a wet interface on a portion of the solid and the sequestrant system is required to maintain the dispensing stability such that the TAED and active oxygen remain unreacted in the solid formulation over time to permit the multi-dosing of the solid compositions.

The first step determines the peracid content by iodometric titration while suppressing the hydrogen peroxide oxidative property by dilution and cold temperatures (ice water). The presence of ice in the reaction flask does not interfere with the titration chemistry. This method does not distinguish between various types of peracids; it measures the total content of all peracids present. The second step uses the same sample and measures hydrogen peroxide content by the addition of sulfuric acid and molybdenum catalyst. These two reagents rapidly accelerate the hydrogen peroxide oxidation of iodide. The hydrogen peroxide concentration is determined by taking the difference between the volume of titrant used for the peracid endpoint and the volume required to reach the hydrogen peroxide endpoint.

Table 3 shows the percentage available oxygen (AO) and peracetic acid (PAA) at each time measurement during the experiment to assess for hourly dispensing. The measurements of greater than 80% remaining oxygen and peracetic acid indicates there is sufficient TAED surviving unreacted in the solid compositions to generate the desired level of peracetic acid for efficient bleaching and/or sanitizing efficacy according to the invention. The results for hourly dispensing show benefits for the control and formulations according to the invention; significant improvements with the compositions employing the present invention are shown when dispensing times increase, such as daily dispensing (Table 4 below).

TABLE 3

| | Formulations Tested | | | | | |
|---|---|---|---|---|---|---|
| Time | % AO of Nominal Value | | | % PAA of Nominal Value | | |
| (hrs) | 1 | 2 | 3 | 1 | 2 | 3 |
| Initial | 89.8 | 96.3 | 96.6 | 90.6 | 86.8 | 84.4 |
| 1 | 82.0 | 92.8 | 94.1 | 84.6 | 91.3 | 89.2 |
| 2 | 76.2 | 93.6 | 92.7 | 74.7 | 88.7 | 93.2 |
| 3 | 89.6 | 90.4 | 96.5 | 95.5 | 90.1 | 93.6 |
| 4 | 87.5 | 93.4 | 93.0 | 90.5 | 91.4 | 88.1 |
| 5 | 89.2 | 94.9 | 95.9 | 82.1 | 102.1 | 95.2 |
| 6 | 91.3 | 95.7 | 91.7 | 88.7 | 87.6 | 88.9 |
| 7 | 88.8 | 94.2 | 92.1 | 91.1 | 88.9 | 88.3 |

Table 4 shows the percentage available oxygen (AO) and peracetic acid (PAA) at each time measurement during the experiment to assess for daily dispensing. The measurements of greater than 80% remaining oxygen and peracetic acid indicates there is sufficient TAED surviving unreacted in the solid compositions to generate the desired level of peracetic acid for efficient bleaching and/or sanitizing efficacy according to the invention.

TABLE 4

| | Formulations Tested | | | | | |
|---|---|---|---|---|---|---|
| Time | % AO of Nominal Value | | | % PAA of Nominal Value | | |
| (days) | 1 | 2 | 3 | 1 | 2 | 3 |
| Initial | 87.5 | 94.4 | 97.3 | 88.9 | 90.3 | 93.8 |
| 1 | 88.4 | 94.0 | 92.1 | 90.3 | 91.0 | 89.9 |
| 2 | 80.2 | 94.7 | 94.3 | 83.7 | 90.5 | 94.8 |
| 3 | 85.9 | 96.4 | 91.3 | 85.4 | 87.4 | 84.6 |
| 4 | 81.3 | 97.1 | 89.8 | 78.6 | 95.8 | 89.7 |

As shown in Tables 3 and 4, both Formulations 2 and 3 outperform the control formulation (Formulation 1) in terms of maintaining available oxygen level and therefore the generated peracetic acid level over time to reflect extended multi-dosing of the solid compositions. The remaining available oxygen levels in the solid formulations are indicative of sufficient stability to retain cleaning, sanitizing and/or bleaching efficacy of the active oxygen compositions according to the invention, as retained active oxygen concentration is required to provide the cleaning, sanitizing and/or bleaching desired for various applications of use.

Example 2

In addition to the dispensing stability testing of the formulations set forth in Example 1, further evaluation of the solid formulations was evaluated pursuant to self-accelerating decomposition temperature (SADT) methodology to determine elevation of temperatures during storage. SADT is known for use in classification of the product according to UN recommendations for the transport of reactive goods. SADT testing monitoring was conducted for the shrink-wrapped 3 lb. solid block formulations in an oven at 60° C. for at least 7 days.

A ⅛" drill bit was employed to drill a hole into the center of each pressed block wrapped in a polyethylene film shrink wrap, which was then placed in an oven at the desired temperature. A temperature probe (thermocouple) was placed into the hole in the block and an additional temperature probe was placed in the oven to monitor the oven temperature. Data was collected with temperature monitoring software. A sample was removed from the oven if any temperature measurement exceeded the oven temperature by more than 6 degrees, which is indicative of the formulation said to be at or above its SADT temperature within 7 days of storage at that temperature.

The SADT studies were conducted to assess the impact of water in the formulations containing the sequestrant system and binding system according to the invention on the stability of the stabilized solid activated bleach compositions. The formulation evaluated are shown in Table 5 representing pressed formulations with and without added water.

TABLE 5

| | Formulation wt-% | | |
|---|---|---|---|
| Raw Material | 4 | 5 | 6 |
| Dense Soda Ash | 20-40 | 20-40 | 20-40 |
| Sodium Chloride | 5-10 | 5-10 | 5-10 |
| Citric Acid | 5-10 | 5-10 | 5-10 |
| Sodium carboxymethyl cellulose | 1-5 | 1-5 | 1-5 |
| Hydroxyethylidene Diphosphonic Acid | 0.1-1 | 0.1-1 | 0.1-1 |
| Sodium Percarbonate | 25-50 | 25-50 | 25-50 |
| Dodecyl benzene sulfonic acid | 1-5 | 1-5 | 1-5 |
| Tetraacetylethylenediamine | 10-25 | 10-25 | 10-25 |
| Water | 0 | 0.5 | 1 |

As shown in FIG. 1, during the storage time the block temperatures for Formulations 4A and 4B (same formulation tested in separate block solids) stayed at or very near to the oven temperature with very little deviation. The Formulations 5A and 5B (containing water in the formulation) did not pass the stability testing, as the formulation having 0.5 wt-% water in the formulation showed an exothermic reaction within 12 hours of storage, with the temperature slowly dropping to the oven temperature over the 7 days of storage. These results are consistent with unstable formulations, where an exothermic reaction is expected to occur within a block (i.e. spike in temperature) within 12 hours.

The results in FIG. 1 and further depicted in Table 6 show the stabilized solid activated bleach compositions according to the invention are sensitive to water content and requires the reduction below at least 0.5 wt-% (and preferably no water contamination) during processing of the formulations.

TABLE 6

| Time | Oven | Formulations | | | |
|---|---|---|---|---|---|
| (hrs) | Temp | 4A | 4B | 5A | 5B |
| 0 | 59.8 | 59.1 | 60.1 | 60.6 | 60.9 |
| 1 | 56.5 | 22.5 | 23.2 | 23.4 | 24.4 |

TABLE 6-continued

| Time | Oven | Formulations | | | |
|---|---|---|---|---|---|
| (hrs) | Temp | 4A | 4B | 5A | 5B |
| 2 | 59.3 | 40.3 | 40.8 | 42.9 | 44.3 |
| 3 | 59.8 | 52.2 | 52.3 | 54.6 | 55 |
| 4 | 60.1 | 57.1 | 57.2 | 60.1 | 60 |
| 5 | 60.2 | 59.2 | 59.3 | 62.4 | 62 |
| 6 | 60.3 | 60.1 | 60.1 | 63.2 | 62.8 |
| 7 | 60.2 | 60.3 | 60.4 | 63.4 | 63 |
| 8 | 60.2 | 60.4 | 60.5 | 63.4 | 63 |
| 9 | 60.2 | 60.4 | 60.5 | 63.3 | 62.9 |
| 10 | 60.2 | 60.4 | 60.6 | 63.2 | 62.8 |
| 11 | 60.2 | 60.4 | 60.6 | 63.1 | 62.7 |
| 12 | 60.3 | 60.5 | 60.6 | 63 | 62.7 |
| 13 | 60.3 | 60.5 | 60.6 | 63 | 62.6 |
| 14 | 60.2 | 60.3 | 60.5 | 62.8 | 62.5 |
| 15 | 60.2 | 60.3 | 60.5 | 62.8 | 62.4 |

The data indicates the self-accelerating decomposition temperature of the stabilized solid activated bleach compositions according to the invention is greater than 60° C., which is well above the expected temperature that the compositions would be exposed to during transportation and storage. The additional 60° C. testing of stabilized solid activated bleach compositions according to the invention with the addition of water (0.5 wt-% contamination in Formulations 5A, 5B) demonstrates the criticality of removing water contamination during processing of the stabilized solid activated bleach compositions.

Table 7 shows the percentage available oxygen (of theoretical value of percarbonate available oxygen remaining in the solid) at each time measurement during the experiment. The measurements of both 40° C. and 50° C. provide accelerated proof of formulation stability, wherein a percentage of remaining available oxygen of approximately 90% or greater is indicative of shelf stability at room temperature for at least one year.

TABLE 7

| Formulation | Initial - RT | 4 weeks - 40° C. | 4 weeks - 50° C. | 8 weeks - RT | 8 weeks - 40° C. | 8 weeks - 40° C. |
|---|---|---|---|---|---|---|
| 4 | 99.21 | 100.99 | 102.04 | 100.17 | 99.86 | 96.53 |
| 5 | 97.67 | 96.31 | 85.21 | 98.41 | 96.69 | 85.01 |
| 6 | 98.97 | 91.91 | 80.51 | 97.27 | 93.56 | 74.64 |

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A stabilized solid activated bleach composition comprising:
   from about 10 wt-% to about 80 wt-% of at least one alkaline solidification matrix;
   from about 10 wt-% to about 75 wt-% of an active oxygen source;
   from about 0.1 wt-% to about 50 wt-% of a bleach activating agent; and from about 0.01 wt-% to about 25 wt-% of a sequestrant system comprising a phosphonate and/or acid thereof;
from about 0.1 wt-% to about 25 wt-% of a binding system consisting of an anionic surfactant and a cellulose component; wherein the binding system and the active oxygen source are in a homogenous mixture; or wherein the binding system and the bleach activating agent are in a homogenous mixture;
wherein the solid composition has less than 1 wt-% water and provides dispensing stability at room temperature for at least about one year, and the active oxygen source and bleach activating agent remains unreacted in the solid composition until a point of use or dilution; and
wherein the solid composition is a pressed solid.

2. The composition according to claim 1, wherein the sequestrant system is a phosphonic acid, dipicolinic acid or a mixture thereof.

3. The composition according to claim 1, wherein the alkaline solidification matrix is an alkali metal carbonate and provides a pH in use solution of at least about 8.5.

4. The composition according to claim 1, wherein the active oxygen source is a peroxygen compound, peroxygen compound adduct, hydrogen peroxide, a hydrogen peroxide liberating or generating compound, inorganic or organic peroxyacid, peroxycarboxylic acid, percarbonate or combinations thereof.

5. The composition according to claim 1, wherein the active oxygen source is an alkali metal percarbonate.

6. The composition according to claim 1, wherein the bleach activating agent is tetraacetyl ethylene diamine.

7. The composition according to claim 1, wherein the anionic surfactant of the binding system is an anionic sulfate surfactant and the cellulose component of the binding system is a carboxymethyl derivative of cellulose.

8. The composition according to claim 1, wherein the anionic surfactant of the binding system is an alkylbenzene sulfonic acid, linear alkylbenzene sulfonate (LAS), or mixture thereof and the cellulose component of the binding system is carboxy methyl cellulose.

9. The composition of claim 1, wherein a use solution of the stabilized solid bleach composition has a pH of between about 8.5 and about 11.5.

10. The composition according to claim 1, further comprising a chelant, additional sequestrants, additional functional ingredient, or mixture thereof.

11. The composition according to claim 1, comprising about 10-70 wt-% of the alkaline solidification matrix, about 1-50 wt-% of the bleach activating agent, about 10-50 wt-% of an active oxygen source, about 0.1-20 wt-% of the sequestrant system, and about 1-15 wt-% of the binding system, wherein the anionic surfactant comprises about 0.1-5 wt-% of the composition and the cellulose source comprises about 1-10 wt-% of the composition.

12. The stabilized solid activated bleach composition of claim 1,
wherein the sequestrant system is phosphonic acid, dipicolinic acid or a mixture thereof; and
wherein the binding system comprising of an anionic sulfate surfactant and a cellulose source,
wherein the cellulose source is a carboxymethyl derivative of cellulose, and wherein the ratio of the anionic sulfate surfactant to the cellulose source is from about 2:1 to about 1:2.

13. The composition according to claim 12, wherein the alkaline solidification matrix is an alkali metal carbonate and provides a use solution of the composition with a pH of between about 9 and about 11.

14. The composition according to claim 12, wherein the active oxygen source is a peroxygen compound, peroxygen compound adduct, hydrogen peroxide, a hydrogen peroxide liberating or generating compound, inorganic or organic peroxyacid, peroxycarboxylic acid, percarbonate and combinations thereof, wherein the bleach activating agent is tetraacetyl ethylene diamine, and wherein the anionic sulfate surfactant is dodecylbenzene sulfonic acid (DDBSA), linear alkylbenzene sulfonate (LAS), or a mixture thereof.

15. The composition according to claim 12, comprising about 15-60 wt-% of the alkalinity solidification source, about 5-40 wt-% of the bleach activating agent, about 20-50 wt-% of an active oxygen source, from about 0.1-1 wt-% of the sequestrant system, and about 1-15 wt-% of the binding system, wherein the anionic surfactant comprises about 0.1-5 wt-% of the composition and the cellulose source comprises about 2-10 wt-% of the composition.

16. A method of cleaning, sanitizing and/or bleaching comprising:
providing the stabilized solid activated bleach composition of claim 1;
generating a use solution of the composition; and
contacting a surface or object in need of cleaning, sanitizing and/or bleaching with the use solution of the composition.

17. The method according to claim 16, wherein the use solution of the composition is employed in a laundry, warewashing, pulp and/or paper bleaching, wastewater treatment and/or epoxidation reaction application of use.

18. The method according to claim 16, wherein the stabilized solid activated bleach composition maintains dispensing stability at room temperature for at least one year.

19. The method according to claim 16, wherein the stabilized solid activated bleach composition comprises about 10-80 wt-% of the alkaline solidification matrix, about 0.1-50 wt-% of the bleach activating agent, about 10-75 wt-% of an active oxygen source, about 0.1-1 wt-% of the sequestrant system, and about 1-15 wt-% of the binding system, wherein the anionic surfactant comprises about 0.1-5 wt-% of the composition and the cellulose source comprises about 2-10 wt-% of the composition.

* * * * *

UNITED STATES PATENT AND TRADEMARK OFFICE
CERTIFICATE OF CORRECTION

PATENT NO. : 10,280,386 B2  
APPLICATION NO. : 14/678055  
DATED : May 7, 2019  
INVENTOR(S) : David Dotzauer et al.

Page 1 of 1

It is certified that error appears in the above-identified patent and that said Letters Patent is hereby corrected as shown below:

<u>In Column 30, Claim 12, Line 3:</u>
DELETE "comprising" after system
INSERT --consisting-- after system Signed and Sealed this
Third Day of September, 2019

Andrei Iancu
*Director of the United States Patent and Trademark Office*